United States Patent [19]
Fox et al.

[11] Patent Number: 5,486,063
[45] Date of Patent: Jan. 23, 1996

[54] METHOD AND APPARATUS FOR SENSING THE LENGTH OF LABEL OR TAG MEDIA BY DETECTING CHANGES IN RELATIVE THICKNESS

[75] Inventors: Duane M. Fox, Snohomish; Joel A. Schoen, Woodinville, both of Wash.

[73] Assignee: Intermec Incorporated, Everett, Wash.

[21] Appl. No.: 370,089

[22] Filed: Jan. 9, 1995

[51] Int. Cl.$^6$ ............................................. G01N 21/86
[52] U.S. Cl. ....................... 400/708; 400/56; 250/559.27
[58] Field of Search ........................... 400/56, 703, 708, 400/708.1, 711; 250/559, 560, 565, 559.19, 559.27

[56] References Cited

U.S. PATENT DOCUMENTS

| | | | |
|---|---|---|---|
| 5,010,766 | 4/1991 | Typpo | 73/159 |
| 5,188,028 | 2/1993 | Reichel | 101/228 |
| 5,193,918 | 3/1993 | Lohrmann et al. | 400/56 |
| 5,204,537 | 4/1993 | Bennet et al. | 400/56 |

FOREIGN PATENT DOCUMENTS

| | | | |
|---|---|---|---|
| 113967 | 4/1990 | Japan | 400/56 |
| 286152 | 11/1993 | Japan | 400/56 |

*Primary Examiner*—Ren Yan
*Attorney, Agent, or Firm*—M. Michael Carpenter; L. David Rish; Donald A. Streck

[57] ABSTRACT

A method and associated apparatus for determining edges of tags/labels carried by a backing strip over a fixed surface. The method comprises the steps of, disposing a sensor above the fixed surface measuring the distance to a surface passing beneath it and outputting a first signal reflecting the distance; receiving and amplifying the first signal to a usable level second signal and outputting the second signal; and, receiving and comparing changes in the second signal to a pre-established threshold amount and outputting a third signal indicating an edge has been found when the second signal changes more than the pre-established threshold amount. Contacting and non-contacting approaches to accomplishing the measurement are disclosed.

8 Claims, 3 Drawing Sheets

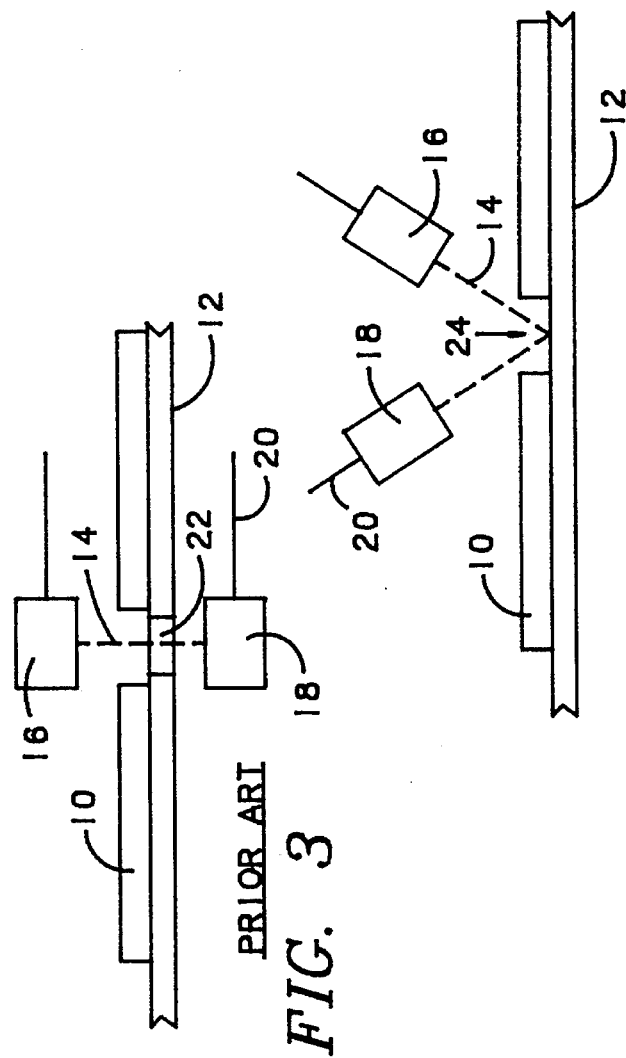
FIG. 2 PRIOR ART
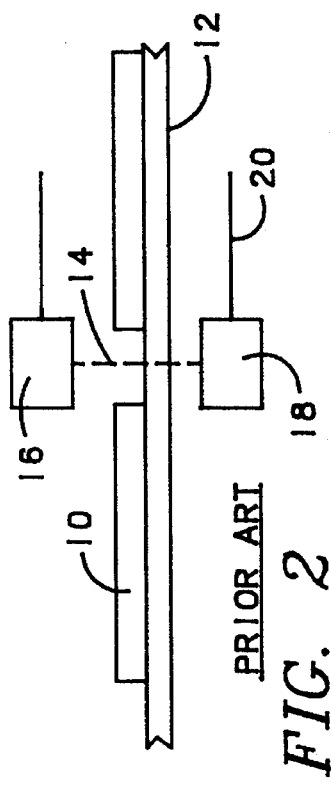
FIG. 3 PRIOR ART
FIG. 4 PRIOR ART
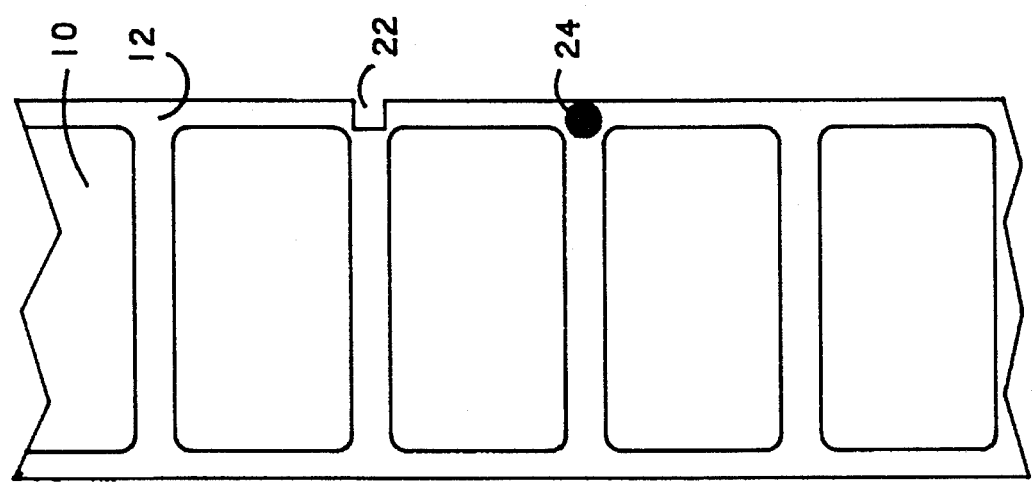
FIG. 1 PRIOR ART

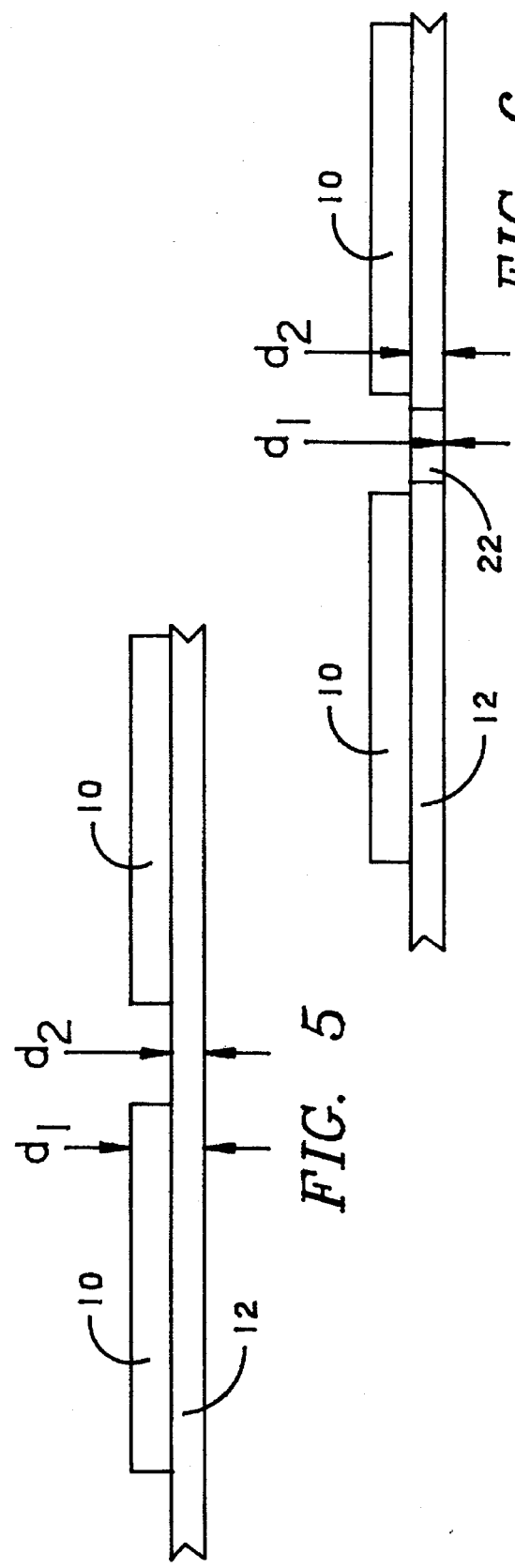
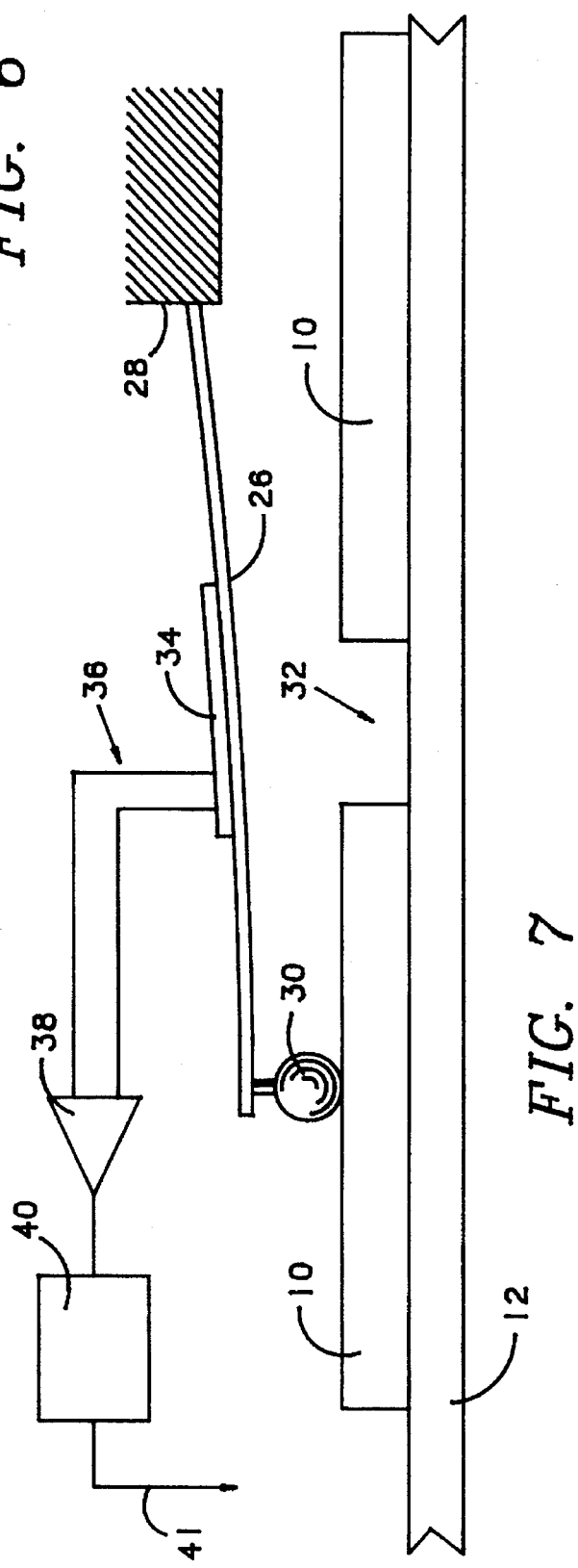

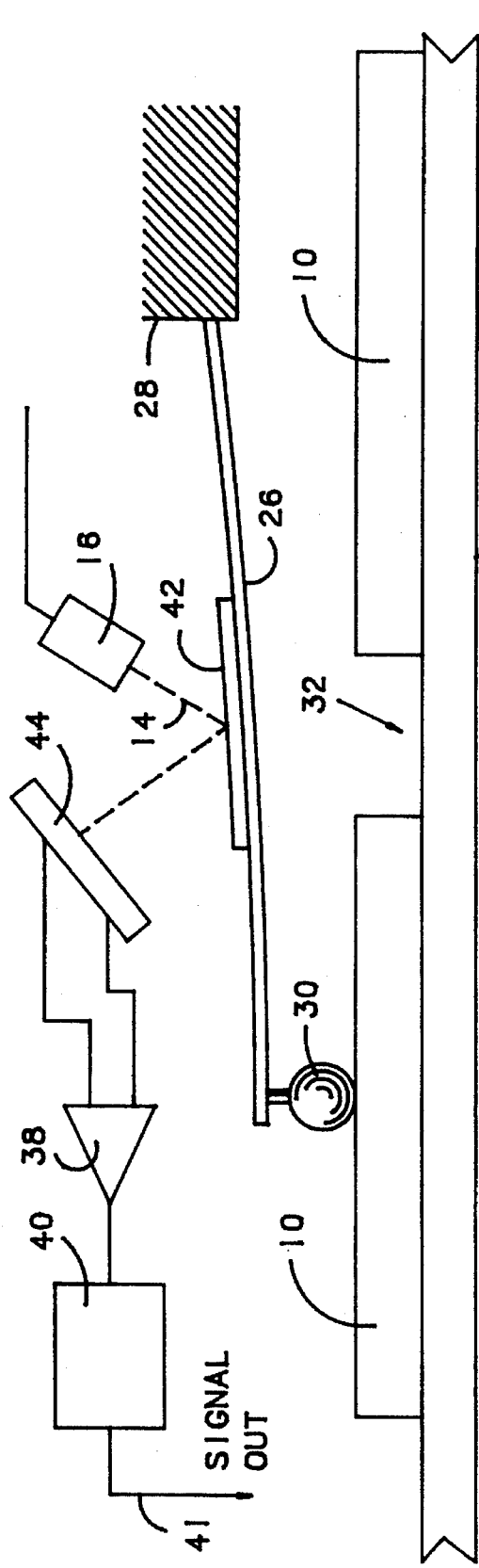
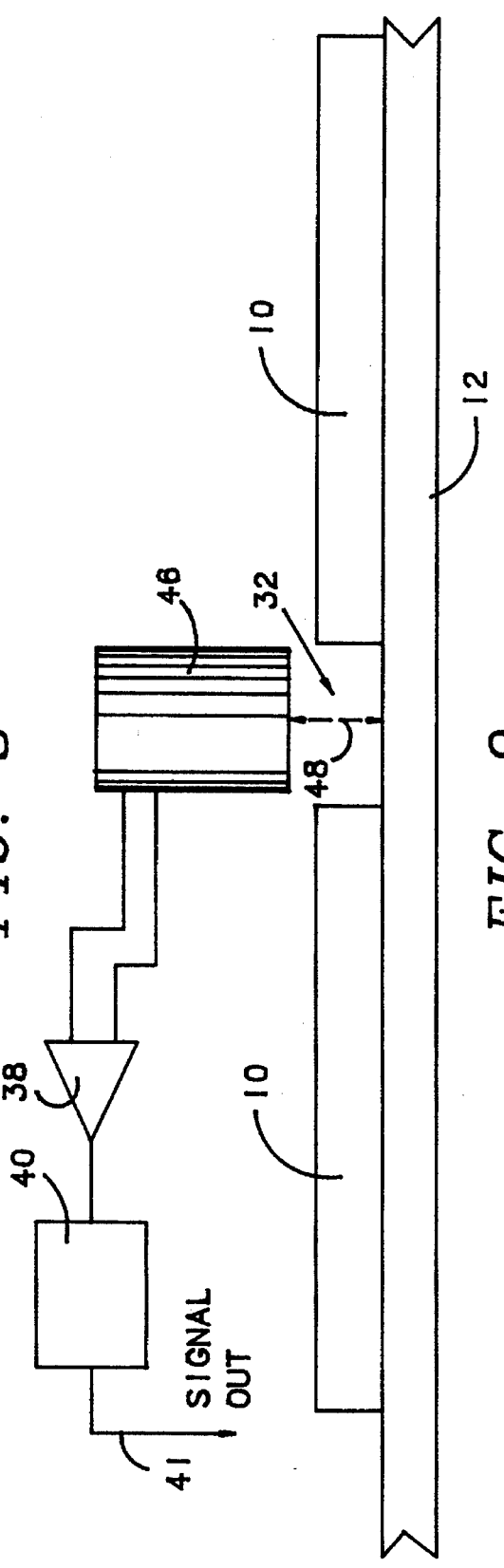
FIG. 8
FIG. 9

5,486,063

METHOD AND APPARATUS FOR SENSING THE LENGTH OF LABEL OR TAG MEDIA BY DETECTING CHANGES IN RELATIVE THICKNESS

BACKGROUND OF THE INVENTION

1. Technical Field

This invention relates to printers printing labels and tags on media and, more particularly, to sensing apparatus for determining edge-indicating changes in thickness of a moving web from a fixed surface over which the web is moving comprising, a sensor disposed above the fixed surface measuring the distance to a surface passing beneath it and outputting a first signal reflecting the distance; an amplifier amplifying the first signal to a usable level second signal; and, a detector sensing changes in the second signal beyond a pre-established threshold amount and outputting a third signal indicating an edge has been found.

2. Background Art

When printing tags or labels removably and adhesively carried by a strip backing, there is a need for the printer to sense the longitudinal position of the tags or labels in order to print on them in proper alignment and subsequently cut between them if the printer includes a cutter mechanism.

The environment is depicted in FIG. 1 and several prior art approaches to solving the problem are shown in FIGS. 2 through 4 in conjunction therewith. The tags/labels 10 are attached to and carried by a strip of backing 12. Typically, there are in the order of 500 or 1,000 tags/labels 10 carried by the strip of backing 12.

In FIG. 2, a light beam 14 from a sending unit 16 is sensed by a receiving unit 18 to produce a signal on line 20 which can be sensed. The receiving unit 18 senses the intensity of the light beam 14 striking it after passing through the tags/labels 10 and strip of backing 12. The signal on the line 20 is supposed to be proportional to the intensity and thereby the amount of material through which the light beam 14 passed. In theory, where the intensity is high, the light beam 14 has not passed through a tag/label 10 so the gap between adjacent ones must be in the path of the light beam 14.

In FIG. 3, the backing 12 contains a notch 22 (or hole) at the location of the gap between adjacent tags/labels 10. The same sending unit 16 sensed by receiving unit 18 again produces a signal on line 20. In this case, however, it is sensing the presence or absence of the backing 12.

In FIG. 4, the light beam 14 from the sending unit 16 to the receiving unit 18 is reflected from the backing 12. A dark or reflective spot 24 is placed at the gap. An increase or decrease in the reflected light beam 14 (depending on whether less reflective or more reflective than the surface of the backing 12) determines the presence of the spot 24 and, therefore, the gap.

The foregoing prior art approaches have proven to be less than desirable due to several factors. The first is the wide range of possible opacity ranges encountered in differing medias. Both the overall opacity and the relative delta opacities can vary widely. Setting light source intensity and amplification gain values that will work for all media is near to impossible. Second, varying ambient light conditions can adversely affect both transmissive and reflective sensor accuracy. Finally, the optical components found in (relatively) low cost sensor pairs vary widely in their light output (IR LEDs) and gain (photo-transistors). These factors must be compensated for in circuit designs and software detection algorithms. These components also exhibit a tendency to drift with age or vary with ambient temperature changes making calibration even more difficult.

Wherefore, it is an object of this invention to provide methods a associated apparatus which will allow gaps between adjacent media items carried by a backing strip to be sensed simply and reliably.

It is an object of this invention to provide methods a associated apparatus which will allow gaps between adjacent media items carried by a backing strip to be sensed in a manner which is not dependent on a constant and repeatable opacity or reflectivity of the measured components.

Other objects and benefits of this invention will become apparent from the description which follows hereinafter when read in conjunction with the drawing figures which accompany it.

SUMMARY OF THE DISCLOSURE

The foregoing objects have been attained by the sensing apparatus of the present invention for determining edge-indicating changes in thickness of a moving web from a fixed surface over which the web is moving comprising, a sensor disposed above the fixed surface measuring the distance to a surface passing beneath it and outputting a first signal reflecting the distance; an amplifier amplifying the first signal to a usable level second signal; and, a detector sensing changes in the second signal beyond a pre-established threshold amount and outputting a third signal indicating an edge has been found.

In a first embodiment, the sensor comprises, a beam fixedly carried above the fixed surface on one end and having a free end in contact with the web, the beam being self-biased to have the free end contact the web for all thicknesses thereof whereby the beam flexes in response to changes in thickness of the web; and, a piezoelectric element carried by the beam to flex therewith, the piezoelectric element having a signal output being the first signal. Preferably, the free end of the beam carries a smooth surfaced element such as a ball or roller which moves over the web without damaging a contacted surface thereof.

In a second embodiment, the sensor comprises, a beam fixedly carried above the fixed surface on one end and having a free end in contact with the web, the beam being self-biased to have the free end contact the web for all thicknesses thereof whereby the beam flexes in response to changes in thickness of the web; a mirror carried by the beam to flex therewith; a light source directing a light beam onto the mirror to be reflected thereby; and, a light sensor positioned to have the light beam impinge on a sensing surface thereof in at least one position of the free end, the light sensor having a signal output being the first signal. In one approach, the light sensor outputs a signal at one thickness of the web and outputs no signal at another thickness of the web. In another approach, the light sensor outputs a signal of a first level at one thickness of the web and outputs a signal of a second level at another thickness of the web. Preferably, the free end of the beam carries a smooth surfaced element such as a ball or roller which moves over the web without damaging a contacted surface thereof.

In a third embodiment, the sensor comprises a transducer emitting a sensing beam onto a surface being measured, the; transducer having a signal output being the first signal. In one implementation, the sensing beam is an ultrasonic beam. In another implementation, the sensing beam is a laser beam.

BRIEF DESCRIPTION OF THE DRAWINGS

FIG. 1 is a drawing of media containing tags or labels thereon and depicting two approaches employed by the prior art to detect the length or spacing of the tags or labels.

FIG. 2 is a simplified side view drawing of the media of FIG. 1 depicting a first prior art approach of sensing relative thickness optically by transmission to determine spacing of the tags or labels.

FIG. 3 is a simplified side view drawing of the media of FIG. 1 depicting a first prior art approach of sensing relative thickness optically by detecting notches to determine spacing of the tags or labels.

FIG. 4 is a simplified side view drawing of the media of FIG. 1 depicting a first prior art approach of sensing relative thickness optically by detecting spots by reflection to determine spacing of the tags or labels.

FIG. 5 is a simplified drawing depicting the general approach of the present invention of measuring the thickness of the media and removable liner to determine spacing of the tags or labels.

FIG. 6 is a simplified drawing depicting the general approach of the present invention of measuring the thickness of the media to detect notches in order to determine spacing of the tags or labels.

FIG. 7 is a simplified drawing showing a first embodiment of the present invention employing a piezoelectric element to detect changes in thickness.

FIG. 8 is a simplified drawing showing a second embodiment of the present invention employing a reflected light beam to detect changes in thickness.

FIG. 9 is a simplified drawing showing a third embodiment of the present invention employing a sonic transducer to detect changes in thickness.

DETAILED DESCRIPTION OF THE PREFERRED EMBODIMENT

As shown in FIGS. 5 and 6, the present invention can be used to measure along the tags/labels 10 or along the backing edge looking for notches 22. In FIG. 5 where measurement is made along the tags/labels 10, the difference in thickness $d_1$ where there is a tag/label 10 and backing 12 in combination and $d_2$ where there is only the backing 12 is what is sensed. In FIG. 6 where measurement is made along the edge away from the tags/labels 10, the difference in thickness $d_1$ where there is no backing 12 (at a notch 22) is sensed as compared to the thickness $d_2$ of the backing 12 away from the notches 22. Note in both cases that the thickness measured is in relation to a fixed bottom surface 13 of the backing 12. Thus, in general, it can be stated that the present invention is directed to measuring the thickness of a moving web above a fixed surface.

A mechanical approach according to the present invention is shown in FIG. 7. A deflection beam 26 is carried at one end by a fixed component 28 of the printer or other device in which the sensing is being implemented. The free end of the beam 26 carries a ball 30, roller, or the like, which is positioned to ride over the surfaces of the tags/labels 10 and backing 12 without injury to those surfaces. The ball 30 (or other shape) is small enough to fall into the gap 32 (or a notch 22). The beam 26 is also self spring biased to urge the ball 30 against those surfaces. One or more piezoelectric film sensors 34 are bonded to the surface(s) of the beam 26 to be flexed in combination therewith. As the beam 26 moves up and down against its self-biasing force, it flexes. As the beam 26 flexes, therefore, the piezoelectric film sensors 34 are flexed and output a signal on the wires 36. The signal on wires 36 is amplified to a usable level at 38 and sensed and detected at 40 using techniques and electronic equipment well known to those of ordinary skill in the art for such purposes. Typically, an edge detector requires a change in signal level beyond a threshold amount so as to only detect true edges and not be confused with ordinary fluctuations in the signal that may occur for various reasons such as not using a regulated power supply in inexpensive equipment for obvious cost reasons. When an edge is detected at 40, a signal is output at 41 to be used by the apparatus using the present invention for its intended purpose therein.

Those of ordinary skill in the art will also recognize and appreciate that the apparatus of FIG. 7 is self calibrating. The piezoelectric film sensors 34 output a spike signal each time they are flexed only. Thus, the detection at 40 needs only to look for a spike and the direction thereof to tell whether the ball 30 has moved up or down from its prior position at an edge.

A variation of the foregoing mechanical sensing approach is shown in FIG. 8. In this case, however, the piezoelectric film sensors 34 are replaced by a reflective mirror 42 carried by the beam 26. A light beam 14 from a sending unit 16 is reflected by the mirror 42 onto a sensor 44. As the beam 26 moves and flexes, the angle of the mirror 42 changes and the light beam 14 is directed to a different point on the sensor 44. The output signal from the sensor 44 is again amplified and sensed/detected. The sensor 44 may be a binary sensor producing an output with the light beam 14 in one position on its sensing surface and producing no output when the light beam 14 is in another position related to the position of the ball 30. It may also be of the type wherein the output signal varies in intensity as a function of the position of the light beam. How to use either type of sensor to accomplish the objects of this invention is well known to those of ordinary skill in the art and will not be addressed in any detail herein in the interest of simplicity.

In a non-contacting approach still according to the present invention as depicted in FIG. 9, a transducer of any of several conventional designs is positioned to direct a sensing beam 48 against the surfaces to be measured. The output signal from the transducer 46 is then evaluated according to well known techniques to determine the distances/thicknesses of interest. For example, the transducer 46 can be an ultrasonic transducer emitting an ultrasonic signal as the sensing beam 48 which measures distances in the manner of a small radar. The transducer 46 could also be a laser-based system in which the number of cycles of a reflected laser beam (as the sensing beam 48) are counted to give a highly accurate measurement of the distance to the surface being measured. The approaches of FIG. 9 are probably more costly to implement than one would normally want to employ within a small label printer and are included primarily for completeness of disclosure purpose. It should be understood, however, that such an approach which is within the scope and spirit of the present invention and intended to be covered by the appended claims could well be financially viable and an approach of choice in large, expensive, commercial, web-processing machinery in which articles carried by the web are to be sensed.

Wherefore, having thus described the present invention, what is claimed is:

1. Sensing apparatus for determining edge-indicating changes in thickness of a moving web from a fixed surface over which the web is moving comprising:

a) a sensor disposed above the fixed surface measuring the distance to a surface passing beneath it and outputting a first signal reflecting said distance;

b) an amplifier amplifying said first signal to a usable level second signal; and, c) a detector sensing changes in said second signal beyond a pre-established threshold amount and outputting a third signal indicating an edge has been found; wherein said sensor comprises:

d) a beam fixedly carried above the fixed surface on one end and having a free end in contact with the web, said beam being self-biased to have said free end contact the web for all thicknesses thereof whereby said beam flexes in response to changes in thickness of the web;

e) a mirror carried by said beam to flex therewith;

f) a light source directing a light beam onto said mirror to be reflected thereby; and, g) a light sensor having a sensing surface positioned to have said light beam reflected by said sensing surface thereof in at least one position of said free end, said light sensor having a signal output being said first signal.

2. The sensing apparatus of claim 1 wherein:

said light sensor outputs a signal at one thickness of the web and outputs no signal at another thickness of the web.

3. The sensing apparatus of claim 1 wherein:

said light sensor outputs a signal of a first level at one thickness of the web and outputs a signal of a second level at another thickness of the web.

4. The sensing apparatus of claim 1 wherein:

said free end of said beam carries a smooth surfaced element which moves over the web without damaging a contacted surface thereof.

5. Sensing apparatus for determining edges of tags/labels carried by a backing strip by measuring changes in thickness from a fixed surface over which the backing strip and tags/labels in combination are moving comprising:

a) a sensor disposed above the fixed surface measuring the distance to a surface passing beneath it and outputting a first signal reflecting said distance, said sensor comprising, a1) a beam fixedly carried above the fixed surface on one end and having a free end in contact with the backing strip and tags/labels, said beam being self-biased to have said free end contact the backing strip and tags/labels for all thicknesses thereof whereby said beam flexes in response to changes in thickness of the backing strip and tags/labels, a2) a mirror carried by said beam to flex therewith, a3) a light source directing a light beam onto said mirror to be reflected thereby, and a4) a light sensor having a sensing surface positioned to have said light beam reflected by said sensing surface thereof in at least one position of said free end, said light sensor having a signal output being said first signal;

b) an amplifier amplifying said first signal to a usable level second signal; and, c) a detector sensing changes in said second signal beyond a pre-established threshold amount and outputting a third signal indicating an edge has been found.

6. The sensing apparatus of claim 5 wherein:

said light sensor outputs a signal at one thickness of the backing strip and tags/labels and outputs no signal at another thickness of the backing strip and tags/labels.

7. The sensing apparatus of claim 5 wherein:

said light sensor outputs a signal of a first level at one thickness of the backing strip and tags/labels and outputs a signal of a second level at another thickness of the backing strip and tags/labels.

8. The sensing apparatus of claim 5 wherein:

said free end of said beam carries a smooth surfaced element which moves over the backing strip and tags/labels without damaging a contacted surface thereof.

\* \* \* \* \*